(12) United States Patent
Axelgaard

(10) Patent No.: US 9,072,884 B2
(45) Date of Patent: Jul. 7, 2015

(54) DIFFERENTIAL DIAMETER ELECTRODE

(75) Inventor: Jens Axelgaard, Fallbrook, CA (US)

(73) Assignee: Axelgaard Manufacturing Company, Ltd., Fallbrook, CA (US)

( * ) Notice: Subject to any disclaimer, the term of this patent is extended or adjusted under 35 U.S.C. 154(b) by 1162 days.

(21) Appl. No.: 11/849,994

(22) Filed: Sep. 4, 2007

(65) Prior Publication Data

US 2009/0062897 A1    Mar. 5, 2009

(51) Int. Cl.
*A61N 1/00* (2006.01)
*A61N 1/04* (2006.01)

(52) U.S. Cl.
CPC .............. *A61N 1/0456* (2013.01); *A61N 1/04* (2013.01); *A61N 1/0452* (2013.01); *A61N 1/0472* (2013.01); *A61N 1/0492* (2013.01)

(58) Field of Classification Search
CPC ............ A61N 1/02; A61N 1/04; A61N 1/18; A61N 1/0404; A61N 1/36014
USPC ......................................... 607/129, 149, 152
See application file for complete search history.

(56) References Cited

U.S. PATENT DOCUMENTS

| | | | |
|---|---|---|---|
| 4,708,149 A * | 11/1987 | Axelgaard et al. | 607/152 |
| 4,722,354 A | 2/1988 | Axelgaard et al. | |
| 4,867,166 A | 9/1989 | Axelgaard et al. | |
| 4,919,148 A * | 4/1990 | Muccio | 607/152 |
| 5,038,796 A | 8/1991 | Axelgaard et al. | |
| 7,392,096 B2 * | 6/2008 | Ferrari | 607/142 |
| 7,769,473 B2 * | 8/2010 | Axelgaard | 607/152 |
| 2005/0148996 A1 * | 7/2005 | Sun et al. | 604/501 |
| 2007/0149001 A1 * | 6/2007 | Uka | 439/67 |

* cited by examiner

*Primary Examiner* — Christopher D Koharski
*Assistant Examiner* — Elizabeth K So
(74) *Attorney, Agent, or Firm* — Hackler Daghighian & Martino

(57) ABSTRACT

A flexible transcutaneous electrical nerve and/or stimulation electrode includes a conductive fabric and a flexible conductive adhesive with a barrier portion surrounding a perimeter of the fabric for preventing extending and/or extendable frays of the fabric from extending exterior to the adhesive. An electrical lead wire interconnects the conductive fabric with an electrical stimulation device and a non-conductive sheet is disposed on another side of the conductive fabric for preventing undesirable electrical contact with the conductive fabric and providing a border seal.

12 Claims, 1 Drawing Sheet

DIFFERENTIAL DIAMETER ELECTRODE

The present invention generally relates to electrodes and, more particularly, to electrodes suitable for transcutaneous nerve and/or muscle stimulation.

Continued development of electrical medical devices has produced a need for a variety of electrodes.

Although many of these electrodes have, as a design objective, good electrical signal transmission between a patient's skin surface and electrical leads interconnected with a device, each has specific requirements dependent upon the type of apparatus for which it is to be used.

As an example, electrocardiograph (EKG) and electroencephalograph (EEG) machines are primarily monitoring type devices which require small contact surfaces, or area, with the patient's skin.

On the other hand, transcutaneous electric nerve stimulation (TENS), and muscle stimulation devices require relatively large skin surface contact to effect such nerve and muscle stimulation.

Transcutaneous electrical nerve stimulation is useful, for example, in post-operative and chronic pain control, while muscle stimulation is useful, for example, in maintaining and development of muscle tissue. Electrodes suitable for use in nerve and muscle stimulation preferably provide a uniform electrical coupling across the skin electrode interface.

As hereinabove noted, electrodes suitable for nerve and/or muscle stimulation may be relatively large having dimensions of several inches or more.

Because muscle stimulation causes muscle contractions, a considerable amount of skin movement is associated therewith.

Additionally, perspiration from the skin is more likely to loosen or disrupt the electrode because of its large size. As should be apparent, the larger the electrode, the longer the evaporation path, or distance, perspiration, occurring at the center regions of the electrode, must travel in order to evaporate, or be released to the atmosphere.

It has been found that prior art electrodes which have been secured to the surface of a patient's skin with medical adhesive tape, or the like, have a tendency to lift off from the skin because of perspiration and movement of the patient's skin during treatment.

Because an electrode suitable for nerve and/or muscle stimulation must provide for an electrical signal to be distributed over the entire surface of the electrode, it must necessarily be conductive.

Prior art electrodes have utilized a number of conductive elements, such as carbon impregnated rubber and vinyl, as well as metallic foils.

However, a useful electrode must be flexible in order to accommodate relative movement of the patient's skin thereebeneath, as hereinabove-described.

Because nerve and muscle stimulation electrodes may be utilized over a long period of time, as may be necessary in connection with sports injuries, the electrode must be compatible with the skin and flex therewith.

Insufficient flexing of the electrode can result in severe irritation of the patient's skin and electrical "hot spots" due to uneven electrode-skin contact, which manifests itself in a rash and a burning sensation.

The sensation of burning may be sensed by the patient within a few minutes after application of electrical signals during nerve and/or muscle stimulation, while the rash conditions generally take a longer period of time to develop.

It has been found that the use of prior art electrodes in nerve and/or muscle stimulation results in a skin rash in up to 25% to 35% of the people undergoing treatment.

An additional problem associated with the necessary stretchability of electrodes utilized in nerve and/or muscle stimulation procedures is that while the electrode must be able to flex, or stretch, in order to accommodate skin movement during treatment, the conductivity of the electrode should not be interrupted, or distorted, due to the stretching of the electrode.

Prior art electrodes have compromised the flexibility of the electrode in an effort to provide uniform current densities over the entire contact area of the electrode. These electrodes typically utilize a metallic mesh, or foil, to provide contactivity of the electrode and utilize a conductive gel between the electrode and the patient's skin in order to accommodate movement therebetween.

There is, however, relative movement between the relatively rigid electrode and the skin, which is accommodated for by the gel. This relative movement oftentimes causes the gel to move from beneath the conductive portion of the electrode, thereby limiting the useful life of the electrode on the skin.

In addition, this relative motion between the skin and the electrode does not provide for the maintenance of the position of the electrode relative to the nerve and/or muscle being stimulated.

Precision positioning of the electrode is, of course, performed by a physician, or the like, knowledgeable in the treatment method. Inaccurate placement of the electrode, or slipping of the electrode from its intended position, may significantly reduce the beneficial effects of the treatment.

U.S. Pat. No. 4,867,166 and U.S. Pat. No. 5,038,796 to Axelgaard, et al. provides a flexible electrode which is able to move with the patient's skin in order to insure proper continuous placement of the electrode relative to the nerve or muscle tissue being stimulated. This electrode utilizes a conductive fabric with a flexible solid conductive adhesive disposed within interstitial areas of the fabric and on one side thereof.

However, during fabrication or during long-term use, frayed ends of the fabric may extend beyond the adhesive which can produce "hot spots" or an "edge bite". The present invention overcomes this problem.

SUMMARY OF THE INVENTION

A flexible transcutaneous electrical nerve and/or muscle stimulation electrode in accordance with the present invention generally includes a conductive fabric comprising conductive fibers for enabling coupling electrical signals to the patient's skin. The conductive fabric generally includes an array of conductive fibers with interstitial areas therebetween.

A flexible conductive adhesive is provided and disposed within the interstitial areas on one side of the conductive fabric for both adhering the electrode to the skin of the patient and providing an electrical conductive contact therebetween.

The adhesive has dimensions greater than corresponding dimensions of the conductive fabric in order to provide a border around the conductive fabric with the border having dimensions greater than any extended or loose threads from a frayed edge of the conductive fabric.

In other words, the conductive adhesive includes a barrier portion, surrounding a perimeter of the fabric, that prevents extending and extendable frays of the fabric from extending exterior to the adhesive. Thus, totally eliminating the possibility of hot spots.

An electrical lead wire is provided that interconnects the conductive fabric and an electrical stimulation device, and a non-conductive sheet is provided and disposed on another side of the conductive fabric for preventing undesirable electrical contact with the conductive fabric. The dimensions of the non-conductive sheet are greater than corresponding dimensions of the adhesive in order to function as a border seal.

It should all be appreciated that the barrier portion of the conductive adhesive also provides a current roll-off safety border.

In one embodiment of the present invention, a second adhesive may be provided for holding a periphery of the non-conductive sheet to a patient's skin.

BRIEF DESCRIPTION OF THE DRAWINGS

The advantages and features of the present invention will be better understood by the following description and drawings in which.

DETAILED DESCRIPTION

Figure 1:
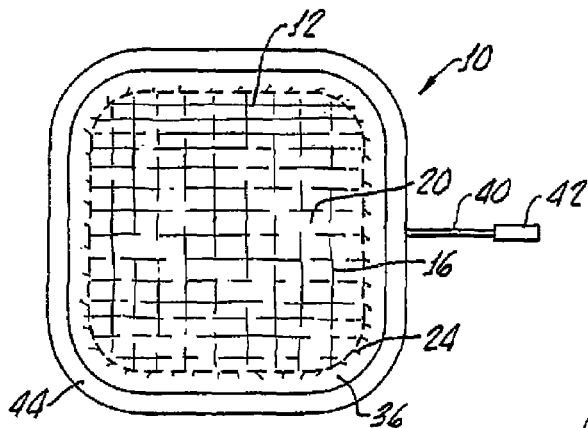
FIG. 1 is a plan view of an electrode in accordance with the present invention generally showing a conductive fabric embedded in a flexible conductive adhesive with a barrier portion of the conductive adhesive surrounding a perimeter of the fabric for preventing extending or extendable frays of the fabric from extending exterior to the adhesive, an electrical lead wire and a nonconductive sheet.
Figure 2:
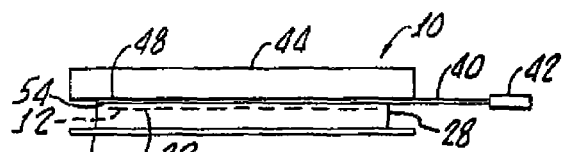
FIG. 2 is a side view of the electrode shown in FIG. 1.

With reference to FIGS. 1 and 2, there is shown a flexible transcutaneous electrical nerve and/or muscle stimulation electrode 10 in accordance with the present invention. Conductive fabric 12, 12A best seen in FIGS. 3 and 3A includes fibers 16, 16A with interstitial areas 20, 20A therebetween. Any suitable conductive fabric 12, 12A may be utilized. As shown, the fabric 12, 12A may have loose ends, or frays, 24, 24A providing a potential for "hot spots" as hereinabove described.

A flexible conductive adhesive 28 of any suitable composition is disposed within the interstitial areas 20 and on one side 32 of the fabric 12, 12A as best seen in FIG. 2. The conductive adhesive 28 provides adherence of the electrode 10 to the skin of the patient (not shown) and provides an electrical conducting contact therebetween. As shown, the adhesive 28 has dimensions greater than corresponding dimensions of the conductive fabric 12, 12A in order to provide a border, or barrier portion, 36 with the border having the dimensions greater than any of the frays 24, 24A as illustrated in FIG. 1.

Thus, this barrier portion 36 prevents any of the frays 24, 24A from extending outside of the adhesive 28 and eliminating any possibility of "hot spots" and providing a current roll-off safety border.

An electrical lead wire 40 interconnects the conductive fabric 12, 12A and includes an adapter, or plug, 42 for interconnection with an electrical stimulation device (not shown). A non-conductive sheet 44 is disposed on another side 48 of the conductive fabric 12, 12A for preventing undesirable electrical contact with the conductive fabric and has dimensions greater than corresponding dimensions of the adhesive in order to function as a border seal. A release liner 50 may be disposed on the adhesive with the release liner 50 being removable in order to expose the adhesive 28 for application to a user's skin (not shown).

The adhesive 28 may be of any suitable configuration and preferably comprise a material of sufficient flexibility to stretch within the interstitial areas and along one side of the conductive fabric 12, 12A to prevent the adhesive 28 from separating from the conductive fibers 16, 16A.

While the non-conductive sheet 44 may be adhered to the fabric 12, 12A through contact with the adhesive 28 through the interstitial areas 20, 20A, a separate pressure sensitive adhesive 54 may be utilized for holding or enhancing adherence of a non-conductive sheet 44 to the conductive fabric 12, 12A and for contacting the electrical lead wire 40 with the conductive fabric 12, 12A. Suitable electrical lead wire 40 includes stranded stainless steel or carbon fiber wires. Materials of construction suitable for use in the present invention are set forth in U.S. Pat. No. 4,867,166 and U.S. Pat. No. 5,038,796 which are to be incorporated herewith in their entirety.

Figure 3:
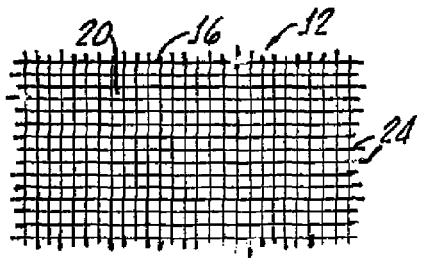
FIG. 3 is an illustration of a woven or non-woven conductive fabric suitable for use in the present invention and also illustrating frayed ends.
Figure 3A:
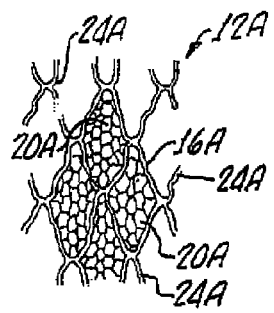
FIG. 3A is an illustration of a knit conductive fabric suitable for use in a present invention and also illustrating frayed ends.
Figure 4:
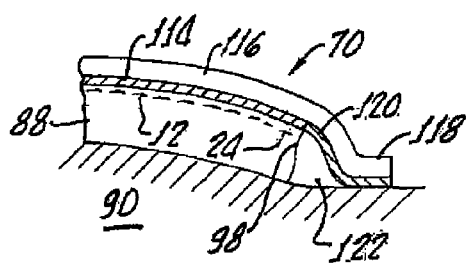
FIG. 4 is a side view of another embodiment of the present invention.

With reference now to FIG. 4, there is shown an alternative embodiment electrode 70 in accordance with the present invention which may include the conductive fabrics 12, 12A, or as illustrated in FIGS. 3 and 3A that includes fibers 16, 16A with interstitial areas 20, 20A therebetween. The fabric 12, 12A typically has loose ends, or frays, 24, 24A providing a potential for "hot spots" as hereinabove described.

A flexible conductive adhesive 88 is disposed within the interstitial areas 20, 20A. As hereinabove noted, the conductive adhesive 88 provides adherence of the electrode 70 to the skin 90 of a patient (not shown) and provides an electrical conducting contact therebetween.

Similar to the electrode 10 shown in FIG. 1, the adhesive 88 has dimensions greater than corresponding dimensions of the conductive fabric 12, 12A in order to provide a border or barrier portion 98 to prevent contact with the frays 24, 24A. An electrical lead wire and plug is provided but not shown in FIG. 4. As with the electrode 10, a separate pressure sensitive adhesive 114 may be utilized for holding or enhancing adherence of a non-conductive sheet 116 to the conductive fabric 12. The non-conductive sheet 116 includes a perimeter 118 and a second pressure sensitive adhesive, preferably a silicone adhesive, 120 is provided for holding the perimeter 118 to the patient's skin (90). In this manner, a moisture barrier 122 is also provided.

Although there has been hereinabove described a specific differential diameter electrode in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A flexible transcutaneous electrical nerve and/or muscle stimulation electrode comprising:
   a conductive fabric comprising conductive fibers for enabling coupling electrical signals to a patient's skin, said conductive fabric comprising an array of the conductive fibers with interstitial areas therebetween, said conductive fabric having a frayed edge with short, loose, or extended threads;

a flexible conductive first adhesive, disposed within said interstitial areas and on one side of said conductive fabric, for both adhering the electrode to the skin of a patient and providing an electrical conducting contact therebetween, the adhesive having dimensions greater than corresponding dimensions of said conductive fabric in order to provide a border around said conductive fabric, said border having dimensions greater than the short loose or extended threads from the frayed edge of said conductive fabric;

an electrical lead wire interconnecting with said conductive fabric and adapted for interconnecting with an electrical stimulation device;

a non-conductive sheet, disposed on another side of said conductive fabric for preventing undesirable electrical contact with the conductive fabric, dimensions of said non-conductive sheet being greater than corresponding dimensions of the adhesive in order to function as a border seal;

a pressure sensitive second adhesive for holding said non-conductive sheet to the conductive fabric and for contacting the electrical lead wire with the conductive fabric; and a silicone and pressure sensitive third adhesive for holding a non-conductive sheet perimeter to the patient's skin, said silicone and pressure sensitive third adhesive being spaced apart from said conductive fabric in order to provide a barrier portion to prevent contact with the frays as well as a moisture barrier.

2. The flexible transcutaneous electrical nerve and/or muscle stimulation electrode according to claim 1 wherein the conductive fibers comprise woven conductive fibers and said flexible conductive adhesive comprises a material of sufficient flexibility to stretch within the interstitial areas and along the one side of the conductive fabric to prevent the flexible conductive adhesive from separating from the conductive fibers.

3. The flexible transcutaneous electrical nerve and/or muscle stimulation electrode according to claim 1 wherein the conductive fibers comprise knit conductive fibers and said flexible conductive adhesive comprises a material of sufficient flexibility to stretch within the interstitial areas and along the one side of the conductive fabric to prevent the flexible conductive adhesive from separating from the conductive fibers.

4. The flexible transcutaneous electrical nerve and/or muscle stimulation electrode according to claim 1 wherein the conductive fibers comprise non-woven conductive fibers and said flexible conductive adhesive comprises a material of sufficient flexibility to stretch within the interstitial areas and along the one side of the conductive fabric to prevent the flexible conductive adhesive from separating from the conductive fibers.

5. A flexible transcutaneous electrical nerve and/or muscle stimulation electrode comprising:

a conductive fabric comprising conductive fibers for enabling coupling electrical signals to a patient's skin, said conductive fabric comprising an array of the conductive fibers with interstitial areas therebetween, said conductive fabric having a frayed edge with short, loose, or extended threads;

a flexible conductive first adhesive, disposed within said interstitial areas and on one side of said conductive fabric, for both adhering the electrode to the skin of a patient and providing an electrical conducting contact therebetween the adhesive encompassing the frayed edge;

a barrier portion of the conductive adhesive, surrounding a perimeter of the fabric, for preventing extending and extendable frays of the fabric from extending exterior to the adhesive;

an electrical lead wire interconnecting with said conductive fabric and adapted for interconnecting with an electrical stimulation device;

a non-conductive sheet, disposed on another side of said conductive fabric for preventing undesirable electrical contact with the conductive fabric, dimensions of said non-conductive sheet being greater than corresponding dimensions of the adhesive in order to function as a border seal;

a pressure sensitive second adhesive for holding said non-conductive sheet to the conductive fabric and for contacting the electrical lead wire with the conductive fabric; and a silicone and pressure sensitive third adhesive for holding a non-conductive sheet perimeter to the patient's skin, said silicone and pressure sensitive third adhesive being spaced apart from said conductive fabric in order to provide a barrier portion to prevent contact with the frays as well as a moisture barrier.

6. The flexible transcutaneous electrical nerve and/or muscle stimulation electrode according to claim 5 wherein the conductive fibers comprise woven conductive fibers and said flexible conductive adhesive comprises a material of sufficient flexibility to stretch within the interstitial areas and along the one side of the conductive fabric to prevent the flexible conductive adhesive from separating from the conductive fibers.

7. The flexible transcutaneous electrical nerve and/or muscle stimulation electrode according to claim 5 wherein the conductive fibers comprise knit conductive fibers and said flexible conductive adhesive comprises a material of sufficient flexibility to stretch within the interstitial areas and along the one side of the conductive fabric to prevent the flexible conductive adhesive from separating from the conductive fibers.

8. The flexible transcutaneous electrical nerve and/or muscle stimulation electrode according to claim 5 wherein the conductive fibers comprise non-woven conductive fibers and said flexible conductive adhesive comprises a material of sufficient flexibility to stretch within the interstitial areas and along the one side of the conductive fabric to prevent the flexible conductive adhesive from separating from the conductive fibers.

9. A flexible transcutaneous electrical nerve and/or muscle stimulation electrode comprising:

a conductive fabric comprising conductive fibers for enabling coupling electrical signals to a patient's skin, said conductive fabric comprising an array of the conductive fibers with interstitial areas therebetween, said conductive fabric having a frayed edge with short, loose, or extended threads;

a flexible conductive first adhesive, disposed within said interstitial areas and on one side of said conductive fabric, for both adhering the electrode to the skin of a patient and providing an electrical conducting contact therebetween, the adhesive having dimensions greater than corresponding dimensions of said conductive fabric including the frayed edge in order to provide a current roll-off safety border;

an electrical lead wire interconnected with said conductive fabric and adapted for interconnection with an electrical stimulation device;

a non-conductive sheet, disposed on another side of said conductive fabric and adhered thereto by the adhesive disposed in said interstitial areas, for preventing undesirable electrical contact with the conductive fabric, dimensions of said non-conductive sheet being greater than corresponding dimensions of the adhesive in order to function as a seal;

a pressure sensitive second adhesive for holding said non-conductive sheet to the conductive fabric and for contacting the electrical lead wire with the conductive fabric; and a silicone and pressure sensitive third adhesive for holding a non-conductive sheet perimeter to the patient's skin, said silicone and pressure sensitive third adhesive being spaced apart from said conductive fabric in order to provide a-barrier portion to prevent contact with the frays as well as a moisture barrier.

10. The flexible transcutaneous electrical nerve and/or muscle stimulation electrode according to claim 9 wherein the conductive fibers comprise woven conductive fibers and said flexible conductive adhesive comprises a material of sufficient flexibility to stretch within the interstitial areas and along the one side of the conductive fabric to prevent the flexible conductive adhesive from separating from the conductive fibers.

11. The flexible transcutaneous electrical nerve and/or muscle stimulation electrode according to claim 9 wherein the conductive fibers comprise knit conductive fibers and said flexible conductive adhesive comprises a material of sufficient flexibility to stretch within the interstitial areas and along the one side of the conductive fabric to prevent the flexible conductive adhesive from separating from the conductive fibers.

12. The flexible transcutaneous electrical nerve and/or muscle stimulation electrode according to claim 9 wherein the conductive fibers comprise non-woven conductive fibers and said flexible conductive adhesive comprises a material of sufficient flexibility to stretch within the interstitial areas and along the one side of the conductive fabric to prevent the flexible conductive adhesive from separating from the conductive fibers.

* * * * *